United States Patent [19]

Fox et al.

[11] Patent Number: 5,493,008
[45] Date of Patent: Feb. 20, 1996

[54] TWO NON-CONTIGUOUS REGIONS CONTRIBUTE TO NIDOGEN BINDING TO A SINGLE EGF-LIKE MOTIF OF THE LAMININ γ1 CHAIN

[75] Inventors: Jay W. Fox, Charlottesville, Va.; Rupert Timpl, Martinsried, Germany

[73] Assignee: The University Of Virginia Patent Foundation, Charlottesville, Va.

[21] Appl. No.: 288,728

[22] Filed: Aug. 15, 1994

[51] Int. Cl.$^6$ .............................. A61K 38/00; C07K 5/00
[52] U.S. Cl. ..................... 530/326; 530/324; 530/327; 530/328; 530/329
[58] Field of Search .................................. 530/324, 326, 530/327, 328, 329

[56] References Cited

PUBLICATIONS

Suzuki, H. et al. (1989) DNA sequence of the *E. coli* K–12 γ-glutamyltranspeptidase gene, ggt. *J. Bacteriol.* 171, 5169–5172. see entire article.

*Primary Examiner*—Jill Warden
*Assistant Examiner*—Benet Prickril

*Attorney, Agent, or Firm*—Oblon, Spivak, McClelland, Maier & Neustadt

[57] ABSTRACT

High affinity binding of nidogen to laminin is mediated by an EGF-like repeat γ1III4 of the mouse laminin γ1 chain and has now been restricted to two short non-contiguous regions of its 56 residue sequence by use of synthetic peptides and recombinant mutants. Disulfide loop a,b of the repeat and a modified loop a,c could completely inhibit binding, with a 5,000-fold or 300-fold reduced affinity, respectively. Synthetic loops c and d lacked inhibitory activity. Some binding contribution of Try819 in loop c was, however, shown by mutation and side chain modification. Together with studies of loop chimeras, this indicated a distinct cooperativity between the two binding sites. The major binding site of loop a was localized to the heptapeptide NIDPNAV (position 798–804). A change of Asp800 to Asn or Ala803 to Val caused a strong reduction in binding activity, while only small effects were observed for the changes Pro801 to Gln and Ile799 to Val. The latter replacement corresponds to the single substitution found in the same region of the Drosophila laminin γ1 chain. However, the changes Asn802 to Ser or Val804 to Ser, both known to exist in the laminin γ2 chain, were deleterious mutations. This demonstrated conservation of binding structure in laminins of distantly related species, but not between homologous chains of laminin isoforms.

12 Claims, 2 Drawing Sheets

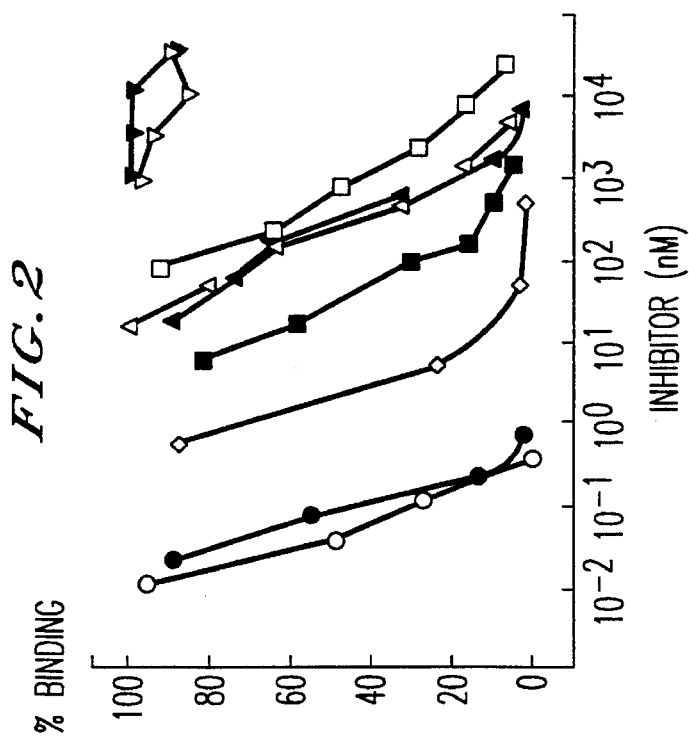
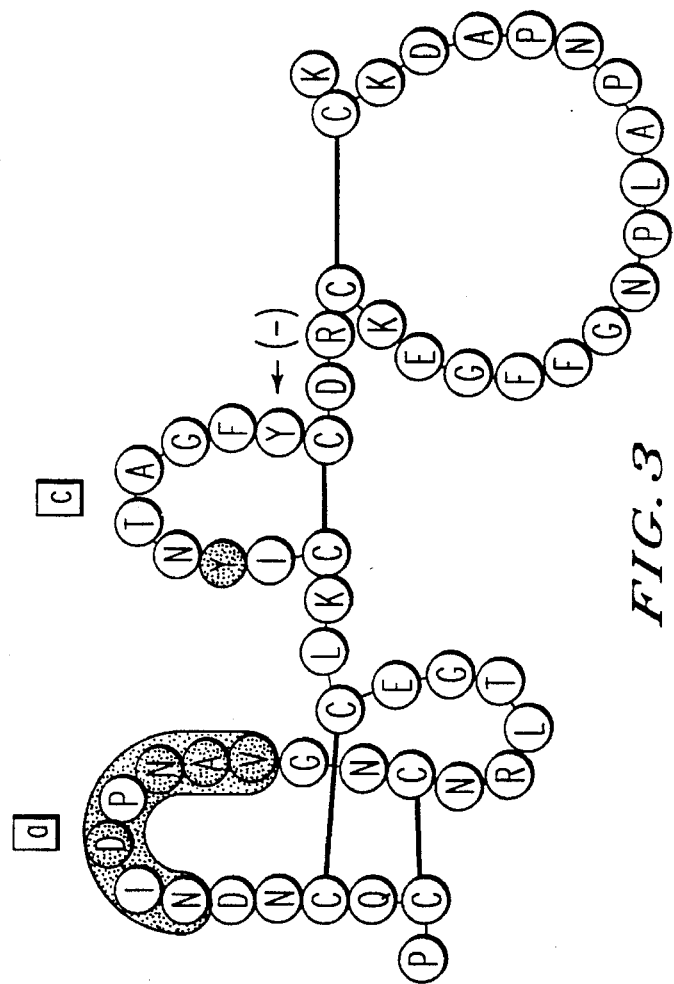

TWO NON-CONTIGUOUS REGIONS CONTRIBUTE TO NIDOGEN BINDING TO A SINGLE EGF-LIKE MOTIF OF THE LAMININ γ1 CHAIN

The present invention is based on work in part funded by the National Institute of Health (R55GM47451).

BACKGROUND OF THE INVENTION

1. Field of the Invention

The present invention relates to peptide antagonists which specifically prevent laminin interaction with nidogen.

2. Background of the Invention

Various isoforms of cross-shaped laminins have been identified as major cell-adhesive and structural proteins of basement membranes and other extracellular structures (Engel, J. (1993), In *Molecular and Cellular Aspects of Basement Membranes,* Rohrbach, D. H. and Timpl, R., (eds), Academic Press, San Diego, Calif., pp. 147–176; Timpl, R. and Brown, J. C. (1994), *Matrix Biol.*). They are large multidomain proteins (600–900 kDa) and consist of disulfide-linked α, β and γ chains (for recent nomenclature see Burgeson, R. E., et al. (1994) *Matrix Biol*, 14, 209–211; Timpl, R. and Brown, J. C. (1994), *Matrix Biol.*). Many heterotypic interaction sites have been demonstrated for laminin 1 of chain composition α1β1γ1, including a single high affinity binding side ($K_D$=0.5 nM) for the 150 kDa basement membrane protein nidogen (Fox, J. W. et al. (1991), *EMBO J.*, 10, 3137–3146). Nidogen also binds to collagen IV, the proteoglycan perlecan and other extracellular ligands and thus mediates the formation of ternary complexes between laminin 1 and other components (Mayer, U. and Timpl, R. (1994) In *Extracellular Matrix Assembly and Structure,* Yurchenco, P. D., Birk, D. and Mecham, R. P. (eds), Academic Press, Orlando, Fla. pp. 389–416; Brown, J. C. et al. (1994), *J. Cell Sci.*, 107, 329–338). Nidogen binding to laminins seems therefore to be a critical step in the supramolecular assembly of basement membranes. This interpretation was recently underscored in studies with antibodies which block the nidogen binding site of laminin 1 (Mayer, U. et al. (1993), *EMBO J.*, 12, 1879–1885) and inhibit kidney tubulogenesis and lung branching in embryonic organ cultures (Ekblom, P. et al (1994) *Development,* 120, 2003–2014).

The high affinity nidogen binding site has been localized to a single motif homologous to epidermal growth factor (EGF) present in the short arm domain III of the mouse laminin γ1 chain (Gerl, M. et al. (1991), *Eur. J. Biochem.*, 292, 167–174; Mayes, U. et al (1993) *EMBO J.*, 12, 1879–1885). This laminin EGF-like repeat γ1III4 consists of 56 residues and of four disulfide-linked loops (a-d), as indicated from the homology to EGF (Cooke, R. M. et al. (1987) *Nature,* 327, 339–341; Montelione, G. T. et al. (1987) *Proc. Natl. Acad. Sci. USA,* 84, 5226–5230) and other representative sequence features (Sasaki, M. and Yamada, Y. (1987), *J. Biol. Chem.*, 262, 17111–17117; Engel, J. (1989), *FEBS Lett.*, 251, 1–7). The same affinity for nidogen binding was also observed with human laminins 2 and 4, of chain compositions α2β1γ1 and α2β1γ1 (Brown, J. C. et al. (1994), *J. Cell Sci.*, 107, 329–338), and is explained by the 97% sequence identity of the mouse and human γ1III4 structure (Pikkarainen, T. et al. (1987), *J. Biol. Chem.*, 263, 6751–6758). A lower sequence identity (61%) has been shown for this repeat in Drosophila laminin γ1 chain (Chi, H. C. and Hui, C. F. (1989), *J. Biol Chem.*, 264, 1543–1550) and the human laminin γ2 chain isoform (77%; Kallunki, P. et al. (1992), *J. Cell Biol.*, 119, 679–693). This has raised the question of whether these laminins also have affinity for nidogen and makes the more precise mapping of binding structures in the mouse repeat γ1III4 necessary for molecular interpretations.

Despite the huge number of EGF-like repeats identified in many extracellular and membrane-bound proteins (see Roes, D. J. G. et al. (1988), *EMBO J.*, 7, 2053–2061; Selander-Sunnerhagen, M. et al. (1992), *J. Biol. Chem.*, 267, 19642–19649), little is known about their binding properties and the structures involved. Biological evidence for the importance of these repeats comes from studies of fibrilin mutants which are considered to cause Marfan syndrome (Dietz H. C. et al. (1991) *Nature,* 352, 337–339; Lee, B. et al. (1991) *Nature,* 352, 330–334) and from lethal mutations in the neurogenic Drosophila protein notch (Kelley, M. R. et al. (1987) *Cell,* 51, 539–548), but the functional basis is not yet understood. A precise identification has, however, been achieved for calcium binding sequences present in loop a and interloop regions of EGF-like repeats from several coagulation factors (Handford, P. A. et al. (1991), *Nature,* 351, 164–167; Selander-Sunnerhagen, M. et al. (1992), *J. Biol. Chem.*, 267, 19642–19649). Site directed mutagenesis was also used to map the receptor binding site of EGF and demonstrated crucial residues at the C-terminal end beyond loop c and in the hinge region between loops b and c (Moy, F. J. et al. (1989), *Proc. Natl. Acad. Sci, USA.*, 86, 9836–9840; Campion, S. R. et al. (1992) *J. Cell Biochem,* 50, 35–42; Campion, S. R. et al. (1993) *Protein Engng.*, 6, 651–659).

In view of the potential importance of nidogen binding to laminin, it is desirable to provide peptide antagonists which inhibit laminin interaction with nidogen.

SUMMARY OF THE INVENTION

Accordingly, one object of the present invention is to provide novel peptide antagonists which inhibit the binding of nidogen to laminin.

A second object of the present invention is to provide a novel peptide antagonist in which the individual residues essential for binding are restricted to non-contiguous regions within a disulfide loop.

The present inventors have now achieved these goals with peptidyl compounds of the formula (I):

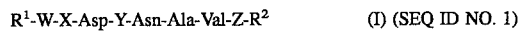

$R^1$-W-X-Asp-Y-Asn-Ala-Val-Z-$R^2$     (I) (SEQ ID NO. 1)

where $R^1$ is hydrogen or a N-terminal protecting group;

$R^2$ is hydrogen, $NH_2$ or a peptidyl group containing 1 to 14 amino acid residues from the N-terminal Leu of the sequence (II):

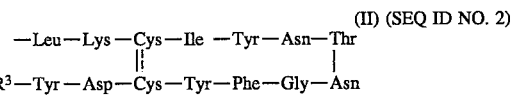

(II) (SEQ ID NO. 2)

W is a valence bond or an amino acid residue;

X is a valence bond or an amino acid residue;

Y is an amino acid residue;

Z is Gly or a peptidyl group containing 1 to 11 amino acid residues of the formula of the sequence (III) (SEQ ID NO. 3):

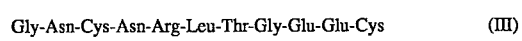

Gly-Asn-Cys-Asn-Arg-Leu-Thr-Gly-Glu-Glu-Cys     (III)

where $R^3$ is hydrogen or an amine such as $NH_2$ or NHMe; and ---- represents the presence or absence of a valence bond.

Various other objects, features and attendant advantages of the present invention will be more fully appreciated as the same becomes better understood from the following detailed description when considered in connection with the accompanying figures.

BRIEF DESCRIPTION OF THE DRAWINGS

FIG. 2 is a graph of the inhibition of radioligand binding between nidogen and laminin fragment P1 by synthetic γ1III peptides and modified fragments. The inhibitors used were laminin fragment p1 (θ), recombinant fragment γ1III3-5 (o), nitrated γ1III3-5 (◊) and synthetic oxidized loop a,b (▲), non-oxidized loop a,b (Δ), oxidized loop c (▼), oxidized loop d (z,901 ), oxidized loop a,c (■) and synthetic NIDP-NAV (SEQ ID NO. 5) (□); and FIG. 3 is a map of the nidogen binding site in the EGF-like repeat γ1III4 of laminin. The relative contribution of individual residues is indicated within the circles and correlate to <10-fold (white circle), a 10- to 100-fold (shaded) and >100-fold (black) loss of affinity if the residues are changed as described in the text. (-) indicates no contribution as judged from site-directed mutagenesis of γ1III4 (SEQ ID NO. 6).

DETAILED DESCRIPTION OF THE PREFERRED EMBODIMENTS

Figure 1:
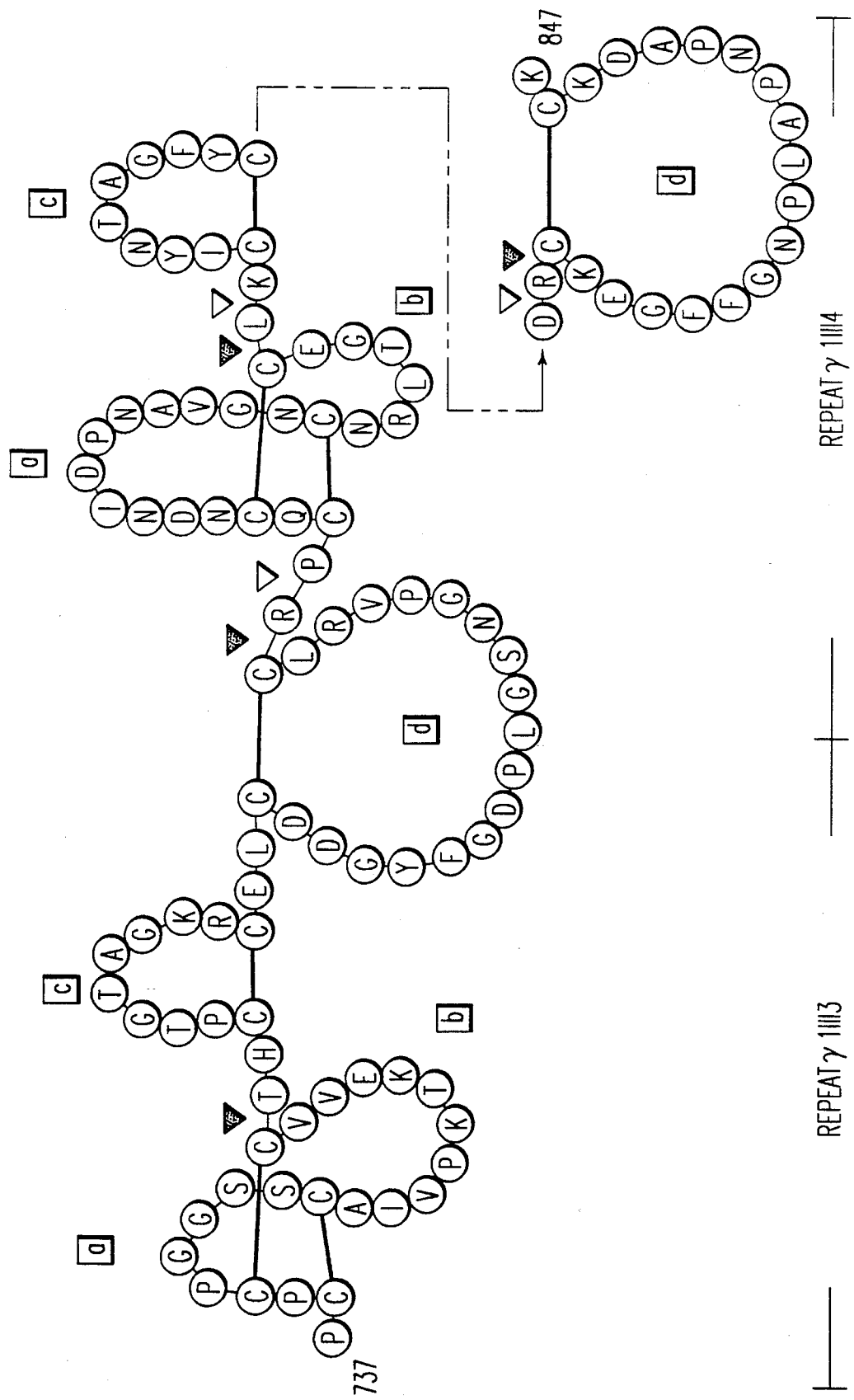
FIG. 1 illustrates the amino acid sequence of EGF-like repeats 3 and 4 in domain III of laminin γ1 chain (SEQ ID NO. 4). Arrowheads mark the borders of synthetic peptides ◁) or of recombinant deletion mutants and chimeras ◀)

The nidogen binding EGF-like repeat 4 of laminin γ1 chain domain III (γIII4) consists of 56 amino acid residues which are folded into four loops (a–d) by disulfide bonds (FIG. 1). This sequence is unique within the γ1 chain (Engel, J. (1993), In *Molecular and Cellular Aspects of Basement Membranes,* Rohrbach, D. H. and Timpl, R., (eds), Academic Press, San Diego, Calif., pp. 147–176), which explains the high specificity found for nidogen binding (Gerl, M., et al. (1991), *Eur. J. Biochem.,* 292, 167–174; Mayer, U. et al. (1993), *EMBO J.,* 12, 1879–1885). It is compared in FIG. 1 with the repeat 3 sequence which was used for chimeric constructs. Since it is likely that not all regions of repeat γ1III4 are equally important for affinity, the present inventors have now more precisely mapped the various binding sites with fragments or mutants which were prepared by peptide synthesis or recombinant methods. Their binding activities were determined in a sensitive radioligand competition assay using authentic laminin fragment P1 or related recombinant fragments as reference inhibitors (FIG. 2).

The binding structure is localized to a single EGF-like motif γ1III4 of laminin (Mayer, U. et al. (1993), *EMBO J.,* 12, 1879–1885). This motif was small enough to approach a more precise identification of binding sites by a combination of recombinant and chemical methods. Disulfide loops a and c of γ1III4 are indispensable for high affinity binding. Each segment alone had either a 5,000-fold reduced affinity (loop a) or an affinity which was too low to measure (loop c). A similar difference was also shown with chimeric constructs, indicating a stronger contribution to binding for loop a than loop c. Furthermore, the connection of loops a and c by an artificial peptide link increased the affinity by a factor 20. This emphasizes that a close spatial relationship between both loops is required for the expression of high binding activity.

The low binding activity of loop a was mapped to the heptapeptide sequence NIDPNAV (SEQ ID NO. 5) (FIG. 3). Synthetic variations of the heptapeptide, as well as chemical modifications, showed a strong contribution to binding of the β-carboxyl group of Asp. The central Asn and C-terminal Val when changed to Ser also caused a considerable loss of activity. The more conservative replacement of Ala by Val still decreased activity by a factor of 16. This indicates that these four residues could provide essential contact sites for nidogen binding. The other three residues, including the N-terminal Asn-Ile and the central Pro, seem to be of much less importance, as shown either by fragmentation or by substitutions. The low contribution of Pro to binding was surprising in view of the abundant evidence that Pro is essential for β turns in loop structures. Yet the binding activity of synthetic loop a was not dependent on disulfide bonds, suggesting that the loop has a more flexible conformation.

Further evidence that loop c is also important for high affinity binding, despite its lack of activity when analyzed as a synthetic product, were derived from chemical modification and recombinant studies. These showed that $Tyr_{819}$, but not $Tyr_{825}$, contributes to binding and its modification caused an ~60-fold reduction in affinity. Replacement of γ1III4 loop c by another loop c from a non-binding EGF-like repeat (fragment γ1III4ab3cd; see Table IV) produced a further 30-fold decrease in activity. This indicates involvement in high affinity binding of other loop c residues, besides $Tyr_{819}$, which remain to be identified. Our fragmentation data also indicate that loop b is not essential for binding.

Based on the above, the present inventors have determined that peptide antagonists with the following minimal sequence (I) (SEQ ID NO. 1) inhibit laminin binding to nidogen:

$$R^1\text{-W-X-Asp-Y-Asn-Ala-Val-Z-}R^2 \quad\quad (I)$$

where $R^1$ is hydrogen or a N-terminal protecting group;

$R^2$ is hydrogen, $NH_2$ or a peptidyl group containing 1 to 14 amino acid residues from the N-terminal Leu of the sequence (II) (SEQ ID NO. 2):

```
   —Leu—Lys—Cys—Ile —Tyr—Asn—Thr         (II)
              ||                |
   R³—Tyr—Asp—Cys—Tyr—Phe—Gly—Asn
```

W is a valence bond or an amino acid residue;

X is a valence bond or an amino acid residue;

Y is an amino acid residue;

Z is Gly or a peptidyl group containing 1 to 11 amino acid residues of the sequence (III) (SEQ ID NO. 3):

$$\text{Gly-Asn-Cys-Asn-Arg-Leu-Thr-Gly-Glu-Glu-Cys} \quad (III)$$

where $R^3$ is hydrogen or an amine such as $NH_2$ or NHME; and ---- represents the presence or absence of a valence bond.

Suitable N-terminal protecting groups useful as $R^1$ in accordance with the present invention include acetyl, benzyl and benzoyl.

Suitable amino acid residues useful in accordance with the present invention include Ala, Asn, Asp, Gly, Val, Leu, Ile, Ser, Thr, Tyr, Cys, Met, Glu, Gln, Arg, Lys, His, Phe, Tyr, Trp, Pro, Hyp (hydroxyproline), Hyl (hydroxylysine), Orn (ornithine) citrulline, homoserine, homocysteine, etc.

W can be a valence bond or any of the above amino acid residues and is preferably Asn, Asp, Gln and Glu; particularly preferably Asn.

X can be any of the above amino acid residues and is preferably Ile, Leu, Ala and Val; particularly preferably Ile.

Y can be a valence bond or any of the above amino acid residues and is preferably Pro, Hyp and Gln; particularly preferably Pro.

In a first embodiment of the present invention the peptide antagonists are flexible and $R^2$ is a peptidyl group containing 1 to 14 amino acid residues from the N-terminal Leu of the sequence (II) (SEQ ID NO. 2):

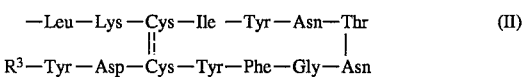

(II)

where $R^3$ is hydrogen or an amine group such as $NH_2$ or NHMe; and ---- represents the absence of a valence bond.

In a second embodiment of the present invention the peptide antagonists are constrained, $R^2$ contains all 15 amino acid residues of the sequence (II) and ---- represents a valence bond.

Z can be a valence bond, Gly or a peptidyl fragment containing 1 to 9 amino acid residues from the N-terminal Gly of the sequence (III) (SEQ ID NO. 3)

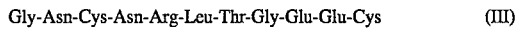

Gly-Asn-Cys-Asn-Arg-Leu-Thr-Gly-Glu-Glu-Cys    (III)

In one embodiment of the present invention, Z is a valence bond. In another embodiment of the present invention, Z is glycine or a peptidyl fragment containing 1 to 9 amino acid residues from the N-terminal Gly of the sequence (III) (SEQ ID NO. 3).

The peptide antagonist of the present invention can be obtained by chemical synthesis or recombinant techniques.

The polypeptides can be chemically synthesized from single amino acids and/or preformed peptides of two or more amino acids in the order of the sequence of the desired polypeptide. Solid-phase or solution methods may be employed. The resultant polypeptide may be converted into a pharmaceutically acceptable salt if desired.

In solid-phase synthesis, the amino acid sequence of the desired polypeptide is built up sequentially from the C-terminal amino acid which is bound to an insoluble resin. When the desired polypeptide has been produced, it is cleaved from the resin. When solution-phase synthesis is employed, the desired polypeptide may again be built up from the C-terminal amino acid. The carboxy group of this acid remains blocked throughout by a suitable protecting group, which is removed at the end of the synthesis.

Whichever technique, solid phase or solution-phase, is employed each amino acid added to the reaction system typically has a protected amino group and an activated carboxyl group. Functional side-chain groups are protected too. After each step in the synthesis, the amino-protecting group is removed. Side-chain functional groups are generally removed at the end of the synthesis.

The peptide antagonists of the present invention may be converted into pharmaceutically acceptable salts. It may be converted into an acid addition salt with an organic or inorganic acid. Suitable acids include acetic, succinic and hydrochloric acid. Alternatively, the peptide may be converted into a carboxylic acid salt such as the ammonium salt or an alkali metal salt such as the sodium or potassium salt.

In order to produce the peptide antagonists of the present invention by recombinant DNA technology, a gene encoding said peptide antagonist is chemically synthesized. The DNA is isolated, purified and inserted into an expression vector.

For expression of the polypeptide, an expression vector is constructed which comprises a DNA sequence encoding the polypeptide and which is capable of expressing the polypeptide when provided in a suitable host. Appropriate transcriptional and translational control elements are provided, including a promoter for the DNA sequence, a transcriptional termination site, and translational start and stop codons. The DNA sequence is provided in the correct frame such as to enable expression of the peptide antagonist to occur in a host compatible with the vector.

The expression vector typically comprises an origin of replication and, if desired, a selectable marker gene such as an antibiotic resistance gene. A promoter is operably linked to the DNA sequence encoding the polypeptide. The expression vector may be a plasmid.

An expression vector capable of expressing the peptide antagonist may be prepared in any convenient fashion. A DNA fragment encoding the polypeptide may be inserted into an appropriate restriction site of an expression vector, for example a plasmid vector.

An expression vector encoding the peptide antagonist is provided in an appropriate host. Cells are transformed with the gene encoding the peptide antagonist. A transformed host is provided under such conditions that the peptide antagonist is expressed therein. Transformed cells, for example, are cultivated so as to enable expression to occur. Any compatible host-vector system may be employed.

The transformed host may be a prokaryotic or eukaryotic host. A bacterial or yeast host may be employed, for example *E. coli* or *S. cerevisiae*. Gram positive bacteria may be employed.

The peptide antagonist that is expressed may be isolated and purified.

The peptide antagonists of the present invention have two major applications, one as a research reagent for in vitro studies of organ development and second as a therapeutic agent for clinical use. As a research reagent, the peptide antagonists of the present invention can be used to obtain models of organ development. For example, preliminary studies have resulted in models of the kidney, lung, salivary and other glands. Such models were obtained by culturing cells in the presence of the peptide antagonists of the present invention. Further models can be obtained by culturing cells with the peptide antagonists of the present invention in combination with tumor cell lines.

The peptide antagonists of the present invention are also useful are therapeutic agents in diabetic patients where basement membrane thickening is a late and often fatal complication which leads to chronic renal failure and blindness (retinopathy). Several other vascular injuries (inlcuding vasculitis, scleroderma, systemic lupus) can also be treated using the peptide antagonists of the present invention.

Tumors often exhibit formation of basement membrane around tumor cells preventing immune cells an antibodies form eliminating these cells. Intravenous injection of the peptides of the present invention would break down these tissues and allow attack by immune cells and antibodies.

The peptide antagonist of the present invention may be administered as a therapeutic agent in an effective amount using any convenient manner such as intravenous administration. The dosage of peptide antagonist to be administered will, of course, be dependent on the size of the patient, the particular disease being treated as well as the severity of the disease. The exact dosage and frequency of administration will depend on clinical responsiveness and other clinical parameters.

Having generally described this invention, a further understanding can be obtained by reference to certain specific examples which are provided herein for purposes of illustration only and are not intended to be limiting unless otherwise specified.

EXAMPLES

Expression of Recombinant EGF-like Repeats

The vectors used to obtain individual or in-tandem arranged repeats γ1III3-5, γ1III3-4, γ1III3 and γ1III4 (γ1III replaces the previously used term B2III; see Burgeson, R. E., et al. (1994), *Matrix Biol*, 14, 209–211) have been described (Mayer, U. et al. (1993), *EMBO J.*, 12, 1879–1885). These vectors and mutated vectors (see below) were used to transfect human embryotic kidney cells 293 and stable transfectants were selected by puromycin or G418 treatment (Nischt, R. et al. (1991), *Eur. J. Biochem.*, 200, 529–536). Stably transfected clones were characterized by Northern hybridization for mRNA expression and by SDS-PAGE of serum-free culture medium to identify clones which efficiently produce and secrete the processed protein (Nischt, R. et al. (1991), *Eur. J. Biochem.*, 200, 529–536). Purification of the recombinant fragments by DEAE-cellulose and molecular sieve chromatography followed previously used protocols (Mayer, U. et al. (1993), *EMBO J.*, 12, 1879–1885).

Construction of Expression Vectors for γ1III4 Mutants

The desired fragment was fused via a NheI site to the signal peptide of human BM-40 to allow processing and secretion of the recombinant product (Mayer, U. et al. (1993), *EMBO J.*, 12, 1879–1885). Mutations, additional restriction sites and stop codons were introduced by primers using PCR amplification with Vent polymerase (Biolabs) following the supplier's instructions. The primers K24, K25, K27 and Ti1 have been described in Mayer, U. et al. {1993), *EMBO J.*, 12, 1879–1885, and the following additional oligonucleotides were used in this study (mutated sequences are underlined):

3ab4S:5'-AAGGAAGTGGTGTGCCTGAAGTGCATC (SEQ ID NO. 7)
3ab4R:5'-GATGCACTTCAGGCACACCACTTCCTT (SEQ ID NO. 8)
4ab3S:5'-GACGGGCGAGTGCACGCACTGTCC (SEQ ID NO. 9)
4ab3R:5'-GGACAGTGCGTGCACTCCCCCGTC (SEQ ID NO. 10)
SYwt:5'-AACACGGCTGGTTTCTAC (SEQ ID NO. 11)
SYmut:5'-AACACGGCTGGTTTCGCCTGCGACCG-GTGC (SEQ ID NO. 12)
RYwt:5'-GAAACCAGCCGTGTTATA (SEQ ID NO. 13)
RYmut:5'-GAAACCAGCCGTGTTAGCGATGCACT-TCAGGC (SEQ ID NO. 14)
Δr:5'-CCGCAGGCTTRGCACAGTCTCACGG (SEQ ID NO. 15)
Δ5:5'-CCGTGAGACTGTCCAAAGCCTGCGC (SEQ ID NO. 16)
N-Mut/R:5'-CAACCGCGCTGGGGTCTATGTTGTC (SEQ ID NO. 17)
Mut-N:5'-ACATAGACCCCAGCGCGGTTGGCAAC (SEQ ID NO. 18)
Mut-D:5'-AACGACAACATAAACCCCAACGCGGT (SEQ ID NO. 19)
Mut-Xba:5'-CGAGCATGCATCATGAGGGCCCTATT (SEQ ID NO. 20)

Construct γ1III3-5 Δ4 was generated by amplification of subfragments from the γ1III3-5 vector with primers TilxΔR or ΔSxK24, fusion of the fragments and amplification with terminal primers TilxK24. Construct γ1III3ab4cd was generated by amplification of fragments from γ1III3-4 with primers Tilx3ab4R and 3ab4SxK27, fusion of fragments and amplification with TilxK27. Construct γ1III4ab3cd was generated by amplification of fragments from γ1III4 with primers Tilx4ab3R and from γ1III3 with primers 4ab3SxK24, fusion and amplification with TilxK25. All fragments were restricted with XbaI and XhoI and cloned into the corresponding sites of expression vector pRC/CMV (Invitrogen).

Mutations of Tyr819 (TAT) and Tyr825 (TAC) to Ala (GCT or GCC) were introduced by PCR amplification of fragments by the use of primers TilxRYmut (resulting in product E1), TilxRYwt (E2). SYmutxK27 (E3) and SywtxK27 (E4). Fragments E1 and E2 were fused in construct γ1III4Y819-A, E2 and E3 were fused in γ1III4Y825-A and both mutations were combined by fusion of E1 and E3 to yield construct γ1III4Y819/825-A. All fused fragments were amplified with primers Til x K27, restricted with XbaI and XhoI and cloned into pRC/CMV.

The construct pRC/D4 was generated by insertion of the HindIII-NorI insert of γ1III4 into the vector pRC/CMV (Invitrogen) and was used alternatively for the expression of this subdomain. Construct γ1III4D800-N contains a mutation of Asp800 (GAC) to Asn (AAC), which was introduced into pRC/D4 according to the transformer mutagenesis system (Clontech). Mutations were introduced by oligonucleotides Mut-D and Mut-Xba and selection for mutated plasmids was by digestion with XbaI as described by the supplier. Correct clones were selected after sequencing of the corresponding region. Construct γ1III4N802-S, containing a mutation of Asn802 (AAC) to Ser (AGC),, was generated from pRC/D4 by amplification with Ty (Biolabs) XN-Mut/R and Mut-NxK27. Fragments were fused, amplified by T7xK27, purified, restricted with NheI and XhoI and inserted into pCis-derived γ1III4, cleaved with NheI and XhoI. All constructs were verified by DNA sequencing of the while insert.

Synthesis and Characterization of Peptides

Synthesis of peptides was carried out on polystyrene solid support using a Biosearch 9600 automated peptide synthesizer system. Amino acids protected with 9-fluoronylmethyloxycarbonyl were pre-activated as N-hydroxybenzotriazole (HOBt) esters that also contained an equimolar amount of 2-(1H-benzotriazole-1-yl)-1.1,3.3-tetramethyluronium tetrafluoroborate and 1.5 equivalents of diisopropyiethylamine in N-methylaminopyrrolidinone: dimethylsulfoxide (3:1). Coupling generally was with a 3-fold molar excess for 2 h (Grant, G. A. (1992) *Synthetic Peptides, A User's Guide*, Freeman and Co., New York, pp. 36–38). A qualitative Kaiser test (Stewart, J. M. and Young, J. D. (1984), *Solid Phase Peptide Synthesis,*, 2nd Edn. Pierce Chemical Company, Rockford, Ill., pp. 105–117) was performed after each coupling to monitor coupling efficiency. Where coupling was incomplete, the amino acid was recoupled using a 6-fold molar excess of preformed symmetric anhydride with diisopropylenbodiimide in methylene chloride (Bodanszky, M. (1984), *Principles of Peptide Synthesis*, Springer, Berlin, pp. 36–39). After 20 min, 3-fold molar excesses of HOB and diisopropylethylamine were added to form an active ester. Coupling continued for another 90 min and the reaction was again tested for completeness. After each coupling, free amino groups were acetylated using 10% acetic anhydride in N-methylpyrrolidinone. Peptides were deprotected and cleaved from the resin with a mixture of 90% trifluoroacetic acid (TFA), 5% thioanisole, 3% ethanedithiol and 2% anisole for 2 h. Following extraction with ether (3X), the peptide was dissolved in 25% acetic acid and desalted by gel filtration on Sephadex G-10 in 50% acetic acid. Pooled aliquots were evaporated to dryness and then rediluted in either water or acetic acid for lyophilization. The dried product was purified by reverse phase HPLC using 0.1% TFA in water and acetonitrile gradients on a C18 column.

Peptides requiring oxidation of a single disulfide were dissolved in aqueous acetic acid to a concentration of <0.1 mg/ml. The pH was adjusted to 8.5 with ammonium hydroxide. The solution was loosely covered, bubbled with air and stirred until oxidation was complete. Completeness of oxidation was determined by Ellman's assay (Stewart, J. M. and Young, J. D. (1984), Solid Phase Peptide Synthesis,, 2nd Edn. Pierce Chemical Company, Rockford, Ill., pp. 105–117) and HPLC. The oxidized material was concentrated, desalted by gel filtration and lyophilized. Peptides requiring a second disulfide were synthesized with a second pair of cysteines protected by an acetamidomethyl (ACM) group. The first oxidation was performed as above. Following lyophilization of the singularly oxidized peptide, the ACM was removed by dissolving the peptide (0.05 nmol) in 350 L methanol : water (1:6). The solution was maintained at room temperature and stirred while adding 50 mL 1 mM iodine in methanol dropwise over 1 h. The solution was cooled and concentrated to remove the methanol. The remaining solution was extracted with chloroform to remove the iodine. An Ellman's assay was performed to ensure completeness. Matrix-assigned laser-desorption ionization time-of-flight mass spectrometry was performed to determine the correct product. Purity was assessed by reversed phase HPLC in several buffer systems.

Chemical and Proteolytic Modifications

Complete reduction of disulfide bonds was performed in 6M guanidine-HCl, 0.05M phosphate buffer, pH 8.0 with 0.02M dithiothreitol (4 h 37° C.) followed by blocking with 0.08M N-ethylmaleimide for 2 h at room temperature. Nitration of tyrosine was accomplished in 0.05M Tris-HCl, pH 8.0, by adding a 2-fold molar excess of tetranitromethane for 1 h at room temperature (Riordan, J. F. and Vallee, B. L. (1972), Methods Enzymol., 25, 515– 521). Selective acetylation of tyrosine hydroxyl groups was done in 1M sodium acetate, pH 5.8 by adding a large excess of acetic acid anhydride for 30 min at room temperature (Onishi, M. et al. (1974), J. Biochem., 76, 7– 13). Selective acetylation of lysine amino groups was achieved in half saturated sodium acetate solution by adding 5×2 μL acetic acid anhydride to 40 mg protein80 ml incubated in an ice bath for 1 h (Fraenkel-Conrat, H. (1957), Methods Enzymol., 4, 247–269). Carboxyl groups (Asp, Glu) were activated with 1-ethyl-3-dimethylaminopropylcarbodiimide and then blocked by norleucine methylester (Hoare, D. G. and Koshland, D. E. (1967), J. Biol. Chem., 242, 2447–2453). For proteolytic cleavage (24 h, 37° C.) in 0.02M $NH_4HCO_3$, trypsin (Worthington) and thermolysin (Merck) were used at a substrate:enzyme ratio of 1:25 and endoproteinase Asp-N (sequencing grade, Boshringer) at a ratio of 1:200. Proteolytic fragments and modified proteins were then purified by reverse phase HPLC and identified by amino acid analysis (Mayer, U. et al. (1991) Eur. J. Biochem., 198, 141–150).

Binding Assay

A radioligand competition assay was used for measurement of relative binding affinities (Mann K. et al. (1988), Eur. J. Biochem., 178, 71–80; Fox, J. W. et al. (1991), EMBO J., 10, 3137–3146). A fixed concentration of recombinant nidogen (0.2 nM) was incubated overnight at 4° C. with inhibitors at varying concentrations, followed by the addition of $^{125}$I-labeled laminin fragment P1 (0.01 nM; 10,000–20,000 c.p.m.) for the same incubation period. Bound and non-bound fragment P1 was then separated by antibodies against nidogen. Competitor concentrations causing 50% inhibition ($IC_{50}$) were determined from dose-response profiles. All assays were calibrated with non-labeled fragment P1, which showed in 14 separate assays an average $IC_{50}$ value (=SD) of 0.05%=0.026 nM. $IC_{50}$ values compared from different assays were normalized to a single fragment P1 value.

Effects of Side Chain Modifications

Previous circumstantial evidence from radioligand assays has indicated that one of the two tyrosines in loop c of repeat γ1III4 contributes to binding (Mayer, U. et al. (1993), EMBO J., 12, 1879–1885). In order to confirm and extend such observations, which could be valuable for the design of mutants, we resorted to several efficient side chain modification procedures. This was done with recombinant fragment γ1III3-5, consisting of repeats 3, 4 and 5, which was available in large quantities. Modification of tyrosine by two different methods caused a 75-fold decrease in binding activity (Table I). A similar decrease was observed after modification of Asp and Glu, while a lower effect (7-fold) was obtained after acetylation of Lys.

TABLE I

Effects of side chain modification of recombinant γ1III3–5 on the inhibitory capability for laminin-nidogen binding

| Modification | $IC_{50}$ (nM) |
| --- | --- |
| None | 0.04 |
| Tyr nitration | 3 |
| Tyr acetylation | 3 |
| Asp/Glu amidation | 2.1 |
| Lys acetylation | 0.27 |

Binding Activity of Synthetic Disulfide Loop Structures and of Smaller Peptides

Three large fragments corresponding to different disulfide loops of repeat γ1III4 were obtained by peptide synthesis (FIG. 1) and the two (loop a,b) or single (loop c and loop d) disulfide bonds of these products were correctly connected by oxidation. Proper disulfide bond formation and deprotection of the purified peptides was assured by mass spectrometry. Competition assays with loop a,b in the oxidized and the non-oxidized forms showed that both could completely inhibit laminin-nidogen binding in an equal fashion. Their $IC_{50}$ values (400 nM) were, however, 5,000-fold higher than that obtained with fragment P1 (Table II).

TABLE II

Inhibitory capacity of synthetic loops of EDG-like repeat 4 and of smaller synthetic and proteolytic fragments

| Origin position | Sequence or equivalent description | IC$_{50}$ (nM) |
|---|---|---|
| Laminin | fragment P1 | 0.08 |
| S, 792–815 | loop a,b, oxidized | 380 |
| S, 792–815 | loop a,b, non-oxidized | 400 |
| S, 792–815 | loop a,b, amidsied | >5,400 |
| S, 816–827 | loop c, oxidized | >200,000 |
| S, 828–847 | loop d, oxidized | >90,000 |
| S, 794–805/ 815–827 | loop a,c, oxidized | 22 |
| S, mixture | loop a,b + loop c | 420 |
| T1, 792–809 | PCQCNDNTDPNAVGNCNR | (SEQ ID NO. 21) 500 |
| T2, 810–815 | LTGECL | (SEQ ID NO. 22) 12,000 |
| Th1, 803–809 | AVGNCNR | (SEQ ID NO. 23) >30,000 |
| E1, 797–815 | DNIDPNAVGNCNRLTGECL | (SEQ ID NO. 24) 530 |
| E2, 800–815 | DPNAVGNCNRLTGECL | (SEQ ID NO. 25) 3,000 |
| E3, 792–796 | PCQCN | (SEQ ID NO. 26) >96,000 |
| S. 798–806 | NIDPNAVGN | (SEQ ID NO. 27) 600 |
| S,˙ 798–804 | NIDPNAV | (SEQ ID NO. 5) 800 |
| S, 799–806 | IOPNAVGN | (SEQ ID NO. 28) 1,600 |
| S, 798–803 | NIDPNA | (SEQ ID NO. 29) >460,000 |

All peptides were synthetic (S) and several obtained by further digestion with trypsin (T), thermolysin (Th) and endoproteinase Asp-N (E). For position numbers and loop identification see FIG. 1.

No inhibitory activity was observed for the oxidized loop c and loop d peptides (IC$_{50}$>90–200 µM). Amidation of loop a,b caused a distinct decrease in activity, in agreement with similar observations for a larger and more active fragment (Table I).

A modified peptide corresponding to loop a,c was also synthesized by deleting the first and third cysteines and seven additional residues from loop b. The first and second pairs of remaining cysteines were then oxidized, yielding the structure QCNDNIDPNAVGCLKC1YNTAGFYCD (SEQ ID NO. 30). This peptide had a 20-fold higher inhibitory activity (IC$_{50}$= 22 nM) compared with loop a,b and was only 300-fold less active than fragment P1 (Table II). This indicates cooperation between binding sites present in loops a and c for high affinity association to nidogen, as already suggested from the tyrosine modification experiments. Cooperation between loops a and c needs a covalent connection, since the activity of loop a,b did not increase upon addition of an equimolar amount of loop c peptide (Table II).

The non-oxidized loop a,b peptide (24 residues) was used in proteolysis experiments to define its binding site (Table II). Cleavage at arginine by trypsin yielded the C-terminal hexapeptide T2, with low activity, and a larger T1 peptide, wit undiminished activity. Thermolysin digestion of T1 released an inactive C-terminal peptide Th1, demonstrating that loop a is responsible for binding.

Cleavage at Asp residues with endoproteinase Asp-N released an inactive N-terminal pentapeptide E3 and a 19 residue peptide E1, with almost unchanged activity (IC$_{50}$= 530 nM). A further cleavage product E2, which lacked the N-terminal sequence Asp-Asn-Ile of E1, showed, however, a significant loss in activity (IC$_{50}$=3 µM).

Together these data suggested that NIDPNAVGN (SEQ ID NO. 27) could be a minimal binding sequence, which was confirmed with a synthetic peptide showing only a marginal loss in activity (IC$_{50}$ =600 nM) when compared with loop a,b (Table II). A further synthetic heptapeptide NIDPNAV (SEQ ID NO. 5) was almost as active (IC$_{50}$=800 nM). Removal of the N-terminal Asn produced, however, a 2-fold loss in activity (IC$_{50}$=1.6 µM). The inhibitory activity was abolished by a larger N-terminal deletion (NID), as well as by removal of the C-terminal Val. This showed that the entire heptapeptide NIDPNAV (SEQ ID NO. 5) (position 798–804 in the γ1 chain) represents the binding site of loop a.

Studies with Synthetic Variants of the Loop a Heptapeptide

The combination of single residues to the inhibitory activity of the heptapeptides was further studied by synthetic homologs containing one to three replacements (Table III). The change of D800 to N produced a 100-fold reduction in activity and is consistent with a comparable loss observed after modification of carboxyl groups (Tables I and II). Surprisingly, the change of P801 to Q caused only a 3-fold decrease. A moderate 16-fold decrease was observed for the conservative A803 to V substitution.

Further replacements were designed from comparison with the homologous laminin sequences. The Drosophila γ1 chain (Chi, H. C. and Hui, C. F. (1989), *J. Biol Chem.*, 264, 1543–1550) shows only a single conservative I799 to V substitution in that heptapeptide region. This substitution, when examined as a synthetic peptide, had only a marginal effect on affinity (Table III). The human laminin γ2 chain isoform (Kallunki, P. et al. (1992), *J. Cell Biol.*, 119, 679–693) shows, in addition to the change found for Drosophila laminin, an N802 to S and V804 to S change. The additional introduction into the heptapeptide sequences of each replacement, separately, or both together, in each case caused inactivation (Table III).

TABLE III

Effects of amino acid replacements in the heptapeptide NIDPNAV on inhibitory capability for laminin-nidogen binding

| Peptide | IC$_{50}$ (nM) |
|---|---|
| NIDPNAV (SEQ ID NO. 5) | 900 |
| NINPNAV (SEQ ID NO. 31) | 100,00 |
| NIDQNAV (SEQ ID NO. 32) | 2,400 |
| NIDPNVV (SEQ ID NO. 33) | 16,000 |
| NVDPNAV (SEQ ID NO. 34) | 1,200 |
| NVDPSAV (SEQ ID NO. 35) | >180,000 |
| NVDPNAS (SEQ ID NO. 36) | >160,000 |
| NVDPSAS (SEQ ID NO. 37) | >290,000 |

Substitutions are shown in bold letters.

Production and Activity of Chimeric Protein Motifs and Site-directed Mutants Previous studies have shown that it is feasible to obtain individual or tandem arrangements of EGF-like repeats of laminin γ1 chain in sufficient quantities from transfected human cell clones as long as the repeats were connected to a signal peptide sequence (Mayer et al. (1993) *EMBO J.*, 12, 1879–1885). The application of the same approach to deletion mutants of the nidogen binding EGF-like repeat lacking either loop d or loop a,b (FIG. 1), however, did not show a corresponding protein product in the culture medium. For several loop d deletion clones we could demonstrate the presence of substantial amounts of specific mRNA by Northern hybridization, suggesting intracellular degradation of their protein product. This indicates that the integrity of the four loop structure is essential for proper folding and secretion.

Chimeras were also provided by exchanging loop a,b and loop c,d mutually between the inactive repeat 3 and the active repeat 4 and had no difficulties in obtaining the corresponding fragments γ1III3ab4cd and γ1III4ab3cd. Further mutants were generated by site-directed mutagenesis and included one or both tyrosines in loop c (fragments γ1III4Y819-A, γ1III4Y825-A and γ1III4Y819/825-A) or residues in loop a (fragments γ1III4D800-N and γ1IIIN802-S), as suggested from the heptapeptide experiments. In addition, we prepared the deletion of a whole EGF-like repeat by joining repeats 3 and 5 (fragment γ1III5-5Δ4). With all these expression constructs the corresponding protein products could be obtained and purified and showed in SDS-gel electrophoresis a single band similar to those described for other recombinant EGF-like repeats (Mayer et al. (1993) *EMBO J.*, 12, 1879–1885). They were all disulfide bonded, as indicated by a decrease in electrophoretic mobility when examined in non-reduced form and by their resistance to pepsin (data not shown).

Inhibition studies with the chimeric fragments (Table IV) demonstrated a distinct decrease in activity for fragment γ1III4ab3cd ($IC_{50}$=80 nM) compared with the wild-type γ1III4 (0.05 nM) and is activity was only 3-fold higher compared with synthetic oxidized loop a,b. An even stronger decrease was noticed for chimeric fragment γ1III3ab4cd, underscoring previous observations on the dual role of the loops a and c in binding. The activities of the chimeras are due to the EGF-like repeat 4, since the deletion mutant γ1III3-5Δ4 was without measurable activity.

TABLE IV

Inhibitory activity of recombinant mutants and chimeric structures of the EGF-like repeat γ1III4 for laminin-nidogen binding

| Inhibitor | $IC_{50}$ (nM) |
| --- | --- |
| Laminin fragment P1 | 0.05 |
| γ1III4 | 0.05 |
| loop a,b oxidized | 270 |
| γ1III4ab3cd | 80 |
| γ1III4ab3cd, reduced | 520 |
| γ1III3ab4cd | 1,100 |
| γ1III3ab4cd, reduced | 6,700 |
| γ1III4Y819-A | 3 |

TABLE IV-continued

Inhibitory activity of recombinant mutants and chimeric structures of the EGF-like repeat γ1III4 for laminin-nidogen binding

| Inhibitor | $IC_{50}$ (nM) |
| --- | --- |
| γ1III4Y825-A | 0.06 |
| γ1III4Y819/825-A | 1.5 |
| γ1III4Y819/825-A, reduced | 430 |
| γ1III4D800,N | 1,000 |
| γ1III4N802-S | 5,500 |
| γ1III3-5Δ4 | >3,200 |

From the three tyrosine mutants studied, only those including Y819 showed a 30- to 60-fold reduction in activity (Table IV). The loss was of the same magnitude as that observed after chemical modification (Table I). The single residue mutation γ1III4Y825-A was, however, without significant effect on inhibitory activity. A dramatic decrease in activity (~100,000-fold) was observed with the mutant γ1III4N802-S, affecting the heptapeptide binding region. Interestingly, this fragment was even 5-fold less active than the chimera γ1III3ab4cd, where the entire loop a,b has been replaced by another, smaller loop structure (see FIG. 1). A further mutation within the heptapeptide region (fragment γ1III4D800-N) showed a similar decrease in activity compared with fragment γ1III3ab4cd (Table IV). These changes correspond to those observed with synthetic variants of the heptapeptide (Table III).

A few selected mutants were reduced and alkylated under denaturing conditions in order to examine the contribution of disulfide bonds to binding activity (Table IV). The largest relative decrease in activity (~300-fold) down to the level of the loop a,b peptide was found for γ1III4Y819/825-A. Reduced γ1III4ab3cd had about the same activity, indicating that loop a,b, when present in a whole EGF-like motif, is to some extent more active in the disulfide-bonded form. Reduction of γ1III3ab4cd caused a further 6-fold decrease in its already rather low activity. The data therefore show some small disulfide dependence of the loops a and c binding regions when examined separately with appropriate recombinant proteins. The high affinity cooperation between both sites seems to be much more dependent, as demonstrated with γ1III4Y819/825-A.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A peptidyl compound of the formula (I) (SEQ ID NO. 1)

$$R^1\text{-W-X-Asp-Y-Asn-Ala-Val-Z-}R^2 \quad (I)$$

where $R^1$ is hydrogen or a N-terminal protecting group;

$R^2$ is hydrogen, $NH_2$ or a peptidyl group containing 1 to 14 amino acid residues from the N-terminal Leu of the sequence (II) (SEQ ID NO. 2):

$$\begin{array}{c}-\text{Leu}-\text{Lys}-\text{Cys}-\text{Ile}-\text{Tyr}-\text{Asn}-\text{Thr}\\ \| \quad\quad | \\ R^3-\text{Tyr}-\text{Asp}-\text{Cys}-\text{Tyr}-\text{Phe}-\text{Gly}-\text{Asn}\end{array} \quad (II)$$

where

W is a valence bond or an amino acid residue;

X is a valence bond or an amino acid residue;

Y is an amino acid residue;

Z is a peptidyl group containing 1 to 9 amino acid residues from the N-terminal Gly of the sequence (III) (SEQ ID NO. 3):

$$\text{-Gly-Asn-Cys-Asn-Arg-Leu-Thr-Gly-Glu-Glu-Cys-} \quad (III)$$

where $R^3$ is hydrogen $NH_2$ or NHME; and ---- represents the presence or absence of a valence bond.

2. The peptidyl compound of claim 1, wherein $R^2$ is hydrogen and Z is Gly.

3. The peptidyl compound of claim 1, wherein W is an amino acid selected from the group consisting of Asn, Asp, Glu and Gln.

4. The peptidyl compound of claim 1, wherein X is an amino acid selected from the group consisting of Ile, Leu and Ala.

5. The peptidyl compound of claim 1, wherein Y is an amino acid selected from the group consisting of Pro and Hyp.

6. The peptidyl compound of claim 1, wherein $R^2$ is a peptidyl group containing 1 to 14 amino acid residues from the N-terminal Leu of the sequence (II) (SEQ ID NO. 2):

$$\begin{array}{c}-\text{Leu}-\text{Lys}-\text{Cys}-\text{Ile}-\text{Tyr}-\text{Asn}-\text{Thr}\\ \| \quad\quad | \\ R^3-\text{Tyr}-\text{Asp}-\text{Cys}-\text{Tyr}-\text{Phe}-\text{Gly}-\text{Asn}\end{array} \quad (II)$$

7. The peptidyl compound of claim 6, wherein $R^2$ is a peptidyl group of the sequence (II) (SEQ ID NO. 2):

$$\begin{array}{c}-\text{Leu}-\text{Lys}-\text{Cys}-\text{Ile}-\text{Tyr}-\text{Asn}-\text{Thr}\\ \| \quad\quad | \\ R^3-\text{Tyr}-\text{Asp}-\text{Cys}-\text{Tyr}-\text{Phe}-\text{Gly}-\text{Asn}\end{array} \quad (II)$$

8. The peptidyl compound of claim 7, wherein Z is a peptidyl fragment containing 1 to 9 amino acids from the N-terminal Gly of the sequence (III) (SEQ ID NO. 3):

$$\text{-Gly-Asn-Cys-Asn-Arg-Leu-Thr-Gly-Glu-Glu-Cys-} \quad (III)$$

where $R^3$ is hydrogen $NH_2$ or NHMe.

9. The peptidyl compound of claim 8, wherein Z is Gly.

10. The peptidyl compound of claim 1, which is $R^1$-Asn-Ile-Asp-Pro-Asn-Ala-Val-$R^3$.

11. The peptidyl compound of claim 1, which is $R^1$-Asp-Pro-Asn-Ala-Val-$R^3$.

12. The peptidyl compound of claim 1, which is (SEQ ID NO. 38)

$$\begin{array}{c}R^1-\text{Asn}-\text{Ile}-\text{Asp}-\text{Pro}-\text{Asn}-\text{Ala}-\text{Val}-\text{Gly}-\text{Leu}-\text{Lys}-\text{Cys}-\text{Ile}-\text{Tyr}-\text{Asn}-\text{Thr}\\ | \quad\quad\quad | \\ R^3-\text{Tyr}-\text{Asp}-\text{Cys}-\text{Tyr}-\text{Phe}-\text{Gly}-\text{Ala.}\end{array}$$

* * * * *

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
            ( A ) NAME/KEY: Modified-site
            ( B ) LOCATION: 1
            ( D ) OTHER INFORMATION: /product="valence bond or any
                        amino acid"
                    / note="may contain an N-terminal protecting group"

( i x ) FEATURE:
            ( A ) NAME/KEY: Modified-site
            ( B ) LOCATION: 2
            ( D ) OTHER INFORMATION: /product="valence bond or any
                        amino acid"

( i x ) FEATURE:
            ( A ) NAME/KEY: Modified-site
            ( B ) LOCATION: 4
            ( D ) OTHER INFORMATION: /product="any amino acid"

( i x ) FEATURE:
            ( A ) NAME/KEY: Modified-site
            ( B ) LOCATION: 8
            ( D ) OTHER INFORMATION: /product="Gly or 1-11 amino acids
                        of SEQ ID NO:3"
                    / note="may be a free carboxy terminus or may be blocked
                        as an amine such as NH2 or NHMe or with 1-14 amino acids
                        from the N- terminal Leu of SEQ ID NO:2"

( x i ) SEQUENCE DESCRIPTION: SEQ ID NO:1:

Xaa  Xaa  Asp  Xaa  Asn  Ala  Val  Xaa
1                      5

( 2 ) INFORMATION FOR SEQ ID NO:2:

( i ) SEQUENCE CHARACTERISTICS:
                ( A ) LENGTH: 14 amino acids
                ( B ) TYPE: amino acid
                ( C ) STRANDEDNESS: single
                ( D ) TOPOLOGY: both ( i x ) FEATURE:
                ( A ) NAME/KEY: Disulfide-bond
                ( B ) LOCATION: 3..12

( i x ) FEATURE:
                ( A ) NAME/KEY: Modified-site
                ( B ) LOCATION: 14
                ( D ) OTHER INFORMATION: /note="carboxy terminus may be
                            hydrogen or protected as an amine such as NH2 or NHMe"

( x i ) SEQUENCE DESCRIPTION: SEQ ID NO:2:

Leu  Lys  Cys  Ile  Tyr  Asn  Thr  Asn  Gly  Phe  Tyr  Cys  Asp  Tyr
1                      5                              10

( 2 ) INFORMATION FOR SEQ ID NO:3:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: linear ( x i ) SEQUENCE DESCRIPTION: SEQ ID NO:3:

Gly  Asn  Cys  Asn  Arg  Leu  Thr  Gly  Glu  Glu  Cys
1                      5                              10

( 2 ) INFORMATION FOR SEQ ID NO:4:

( i ) SEQUENCE CHARACTERISTICS:
                ( A ) LENGTH: 111 amino acids
                ( B ) TYPE: amino acid
                ( C ) STRANDEDNESS: single
                ( D ) TOPOLOGY: linear ( i x ) FEATURE:
    ( A ) NAME/KEY: Disulfide-bond
    ( B ) LOCATION: 2..10

( i x ) FEATURE:
    ( A ) NAME/KEY: Disulfide-bond
    ( B ) LOCATION: 4..21

( i x ) FEATURE:
    ( A ) NAME/KEY: Disulfide-bond
    ( B ) LOCATION: 24..33

( i x ) FEATURE:
    ( A ) NAME/KEY: Disulfide-bond
    ( B ) LOCATION: 36..54

( i x ) FEATURE:
    ( A ) NAME/KEY: Disulfide-bond
    ( B ) LOCATION: 57..71

( i x ) FEATURE:
    ( A ) NAME/KEY: Disulfide-bond
    ( B ) LOCATION: 59..78

( i x ) FEATURE:
    ( A ) NAME/KEY: Disulfide-bond
    ( B ) LOCATION: 81..90

( i x ) FEATURE:
    ( A ) NAME/KEY: Disulfide-bond
    ( B ) LOCATION: 93..110

( x i ) SEQUENCE DESCRIPTION: SEQ ID NO:4:

| Pro | Cys | Pro | Cys | Pro | Gly | Gly | Ser | Ser | Cys | Ala | Ile | Val | Pro | Lys | Thr |
|---|---|---|---|---|---|---|---|---|---|---|---|---|---|---|---|
| 1 | | | | 5 | | | | | 10 | | | | | 15 | |
| Lys | Glu | Val | Val | Cys | Thr | His | Cys | Pro | Thr | Gly | Thr | Ala | Gly | Lys | Arg |
| | | | 20 | | | | | 25 | | | | | 30 | | |
| Cys | Glu | Leu | Cys | Asp | Asp | Gly | Tyr | Phe | Gly | Asp | Pro | Leu | Gly | Ser | Asn |
| | | 35 | | | | | 40 | | | | | 45 | | | |
| Gly | Pro | Val | Arg | Leu | Cys | Arg | Pro | Cys | Gln | Cys | Asn | Asp | Asn | Ile | Asp |
| | 50 | | | | | 55 | | | | | 60 | | | | |
| Pro | Asn | Ala | Val | Gly | Asn | Cys | Asn | Arg | Leu | Thr | Gly | Glu | Cys | Leu | Lys |
| 65 | | | | | 70 | | | | | 75 | | | | | 80 |
| Cys | Ile | Tyr | Asn | Thr | Ala | Gly | Phe | Tyr | Cys | Asp | Arg | Cys | Lys | Glu | Gly |
| | | | | 85 | | | | | 90 | | | | | 95 | |
| Phe | Phe | Gly | Asn | Pro | Leu | Ala | Pro | Asn | Pro | Ala | Asp | Lys | Cys | Lys | |
| | | | 100 | | | | | 105 | | | | 110 | | | |

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

| Asn | Ile | Asp | Pro | Asn | Ala | Val |
|---|---|---|---|---|---|---|
| 1 | | | | 5 | | |

( 2 ) INFORMATION FOR SEQ ID NO:6:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i x ) FEATURE:
        ( A ) NAME/KEY: Disulfide-bond ( B ) LOCATION: 2..15

( i x ) FEATURE:
            ( A ) NAME/KEY: Disulfide-bond
            ( B ) LOCATION: 4..22

( i x ) FEATURE:
            ( A ) NAME/KEY: Disulfide-bond
            ( B ) LOCATION: 25..34

( i x ) FEATURE:
            ( A ) NAME/KEY: Disulfide-bond
            ( B ) LOCATION: 37..53

( x i ) SEQUENCE DESCRIPTION: SEQ ID NO:6:

| Pro | Cys | Gln | Cys | Asn | Asn | Ile | Asp | Pro | Asn | Ala | Val | Gly | Asn | Cys | Asn |
|---|---|---|---|---|---|---|---|---|---|---|---|---|---|---|---|
| 1 | | | | 5 | | | | | 10 | | | | | 15 | |

| Arg | Leu | Thr | Gly | Glu | Cys | Leu | Lys | Cys | Ile | Tyr | Asn | Thr | Ala | Gly | Phe |
|---|---|---|---|---|---|---|---|---|---|---|---|---|---|---|---|
| | | | 20 | | | | | 25 | | | | | 30 | | |

| Tyr | Cys | Asp | Arg | Cys | Lys | Glu | Gly | Phe | Phe | Gly | Asn | Pro | Leu | Ala | Pro |
|---|---|---|---|---|---|---|---|---|---|---|---|---|---|---|---|
| | | 35 | | | | | 40 | | | | | 45 | | | |

| Asn | Pro | Ala | Lys | Cys | Lys |
|---|---|---|---|---|---|
| | 50 | | | | |

( 2 ) INFORMATION FOR SEQ ID NO:7:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

AAGGAAGTGG TGTGCCTGAA GTGCATC                                                                           27

( 2 ) INFORMATION FOR SEQ ID NO:8:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:8:

GATGCACTTC AGGCACACCA CTTCCTT                                                                           27

( 2 ) INFORMATION FOR SEQ ID NO:9:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:9:

GACGGGCGAG TGCACGCACT GTCC                                                                              24

( 2 ) INFORMATION FOR SEQ ID NO:10:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:10:

GGACAGTGCG TGCACTCCCC CGTC                                                                              24

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

AACACGGCTG GTTTCTAC                                                  18

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:12:

AACACGGCTG GTTTCGCCTG CGACCGGTGC                          30

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

GAAACCAGCC GTGTTATA                                                  18

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:14:

GAAACCAGCC GTGTTAGCGA TGCACTTCAG GC                       32

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

CCGCAGGCTT GCACAGTCTC ACGG                                 24

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:16:

CCGTGAGACT GTCCAAAGCC TGCGC                               25

(2) INFORMATION FOR SEQ ID NO:17:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

CAACCGCGCT GGGGTCTATG TTGTC 25

( 2 ) INFORMATION FOR SEQ ID NO:18:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

ACATAGACCC CAGCGCGGTT GGCAAC 26

( 2 ) INFORMATION FOR SEQ ID NO:19:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

AACGACAACA TAAACCCCAA CGCGGT 26

( 2 ) INFORMATION FOR SEQ ID NO:20:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CGAGCATGCA TCATGAGGGC CCTATT 26

( 2 ) INFORMATION FOR SEQ ID NO:21:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( x i ) SEQUENCE DESCRIPTION: SEQ ID NO:21:

Pro Cys Gln Cys Asn Asp Asn Thr Asp Pro Asn Ala Val Gly Asn Cys
1               5                   10                  15

Asn Arg ( 2 ) INFORMATION FOR SEQ ID NO:22:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( x i ) SEQUENCE DESCRIPTION: SEQ ID NO:22:

Leu Thr Gly Glu Cys Leu
1               5

( 2 ) INFORMATION FOR SEQ ID NO:23:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

```
Ala  Val  Gly  Asn  Cys  Asn  Arg
1                   5
```

( 2 ) INFORMATION FOR SEQ ID NO:24:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

```
Asp  Asn  Ile  Asp  Pro  Asn  Ala  Val  Gly  Asn  Cys  Asn  Arg  Leu  Thr  Gly
1                   5                        10                       15
Glu  Cys  Leu
```

( 2 ) INFORMATION FOR SEQ ID NO:25:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

```
Asp  Pro  Asn  Ala  Val  Gly  Asn  Cys  Asn  Arg  Leu  Thr  Gly  Glu  Cys  Leu
1                   5                        10                       15
```

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

```
Pro  Cys  Gln  Cys  Asn
1                   5
```

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:27:

```
Asn  Ile  Asp  Pro  Asn  Ala  Val  Gly  Asn
1                   5
```

( 2 ) INFORMATION FOR SEQ ID NO:28:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:28:

Ile Pro Asn Ala Val Gly Asn
1               5

( 2 ) INFORMATION FOR SEQ ID NO:29:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( x i ) SEQUENCE DESCRIPTION: SEQ ID NO:29:

Asn Ile Asp Pro Asn Ala
1               5

( 2 ) INFORMATION FOR SEQ ID NO:30:

( i ) SEQUENCE CHARACTERISTICS:
    ( A ) LENGTH: 26 amino acids
    ( B ) TYPE: amino acid
    ( C ) STRANDEDNESS: single
    ( D ) TOPOLOGY: linear ( x i ) SEQUENCE DESCRIPTION: SEQ ID NO:30:

Gln Cys Asn Asp Asn Ile Asp Pro Asn Ala Val Gly Cys Leu Lys Cys
1               5                   10                  15

Leu Tyr Asn Thr Ala Gly Phe Tyr Cys Asp
            20                  25

( 2 ) INFORMATION FOR SEQ ID NO:31:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:31:

Asn Ile Asn Pro Asn Ala Val
1               5

( 2 ) INFORMATION FOR SEQ ID NO:32:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:32:

Asn Ile Asp Gln Asn Ala Val
1               5

( 2 ) INFORMATION FOR SEQ ID NO:33:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:33:

Asn Ile Asp Pro Asn Val Val
1               5

( 2 ) INFORMATION FOR SEQ ID NO:34:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( x i ) SEQUENCE DESCRIPTION: SEQ ID NO:34:

Asn Val Asp Pro Asn Ala Val
 1               5

( 2 ) INFORMATION FOR SEQ ID NO:35:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( x i ) SEQUENCE DESCRIPTION: SEQ ID NO:35:

Asn Val Asp Pro Ser Ala Val
 1               5

( 2 ) INFORMATION FOR SEQ ID NO:36:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( x i ) SEQUENCE DESCRIPTION: SEQ ID NO:36:

Asn Val Asp Pro Asn Ala Ser
 1               5

( 2 ) INFORMATION FOR SEQ ID NO:37:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( x i ) SEQUENCE DESCRIPTION: SEQ ID NO:37:

Asn Val Asp Pro Ser Ala Ser
 1               5

( 2 ) INFORMATION FOR SEQ ID NO:38:

( i ) SEQUENCE CHARACTERISTICS:
   ( A ) LENGTH: 22 amino acids
   ( B ) TYPE: amino acid
   ( C ) STRANDEDNESS: single
   ( D ) TOPOLOGY: linear ( i x ) FEATURE:
   ( A ) NAME/KEY: Disulfide-bond
   ( B ) LOCATION: 11..20

( i x ) FEATURE:
   ( A ) NAME/KEY: Modified-site
   ( B ) LOCATION: 1
   ( D ) OTHER INFORMATION: /note="N-terminus can be protected
    with a protecting group"

( i x ) FEATURE:
   ( A ) NAME/KEY: Modified-site
   ( B ) LOCATION: 22
   ( D ) OTHER INFORMATION: /note="C-terminus can be protected
    as an amine such as NH2 or NHMe"

(x i) SEQUENCE DESCRIPTION: SEQ ID NO:38:

```
Asn Ile Asp Pro Asn Ala Val Gly Leu Lys Cys Ile Tyr Asn Thr Ala
1               5                   10                  15

Gly Phe Tyr Cys Asp Tyr
                20
```